United States Patent [19]

Takahashi et al.

[11] 4,341,912
[45] Jul. 27, 1982

[54] PROCESS FOR PRODUCING ALKENYL-SUBSTITUTED AROMATIC COMPOUNDS AND CATALYST THEREFOR

[75] Inventors: Kunimasa Takahashi; Makoto Imanari; Yoshihisa Watanabe, all of Amimachi, Japan

[73] Assignee: Mitsubishi Petrochemical Co. Ltd., Tokyo, Japan

[21] Appl. No.: 57,810

[22] Filed: Jul. 16, 1979

Related U.S. Application Data

[63] Continuation of Ser. No. 837,270, Sep. 27, 1977, abandoned.

[30] Foreign Application Priority Data

Oct. 1, 1976 [JP] Japan .................................. 51-117253

[51] Int. Cl.³ .................................................. C07C 4/02
[52] U.S. Cl. .................................................. 585/443
[58] Field of Search ........................ 585/443, 444, 442

[56] References Cited

U.S. PATENT DOCUMENTS

| | | | |
|---|---|---|---|
| 3,271,469 | 9/1966 | Bloch | 585/442 |
| 3,308,188 | 3/1967 | Bajars | 585/657 |
| 3,651,160 | 3/1972 | Reuss et al. | 585/443 |
| 3,742,078 | 6/1973 | Hayes | 585/444 |
| 3,839,478 | 10/1974 | Gardner | 585/442 |
| 3,900,525 | 8/1975 | Christmann et al. | 585/443 |
| 4,012,337 | 3/1977 | Mitchell | 252/439 |
| 4,070,413 | 1/1978 | Imai | 585/629 |

FOREIGN PATENT DOCUMENTS

| | | | |
|---|---|---|---|
| 2744136 | 4/1978 | Fed. Rep. of Germany | 585/443 |
| 49-39246 | 10/1974 | Japan | 585/443 |
| 50-53333 | 5/1975 | Japan | 585/443 |
| 1098697 | 1/1968 | United Kingdom | 585/443 |
| 1144214 | 3/1969 | United Kingdom | 585/442 |

Primary Examiner—Delbert E. Gantz
Assistant Examiner—Joseph A. Boska
Attorney, Agent, or Firm—Sherman & Shalloway

[57] ABSTRACT

A process for producing an alkenyl-substituted aromatic compound which comprises catalytically reacting an alkyl-substituted aromatic compound in the vapor phase in the presence of molecular oxygen and a catalyst composed of palladium metal and a metal halide compound supported on an alumina carrier to convert it to the corresponding alkenyl-substituted aromatic compound, wherein said reaction is carried out in the presence of a catalyst composed of palladium metal and a metal halide compound supported on a carrier consisting substantially of α-alumina.

18 Claims, No Drawings

PROCESS FOR PRODUCING ALKENYL-SUBSTITUTED AROMATIC COMPOUNDS AND CATALYST THEREFOR

This is a continuation, of application Ser. No. 837,270, filed Sept. 27, 1977, now abandoned.

This invention relates to an improved process for producing alkenyl-substituted aromatic compounds, which comprises oxidatively dehydrogenating an alkyl-substituted aromatic compound in the vapor phase in the presence of a catalyst to convert it to the corresponding alkenyl-substituted aromatic compound in a high selectivity stably for long periods of time while maintaining an excellent catalytic activity and advantageously inhibiting undesirable side-reactions. The invention also relates to an improved catalyst for oxidative dehydrogenation of alkyl-substituted aromatic compounds which is suitable for use in the aforesaid process and which has excellent catalytic activity and a long active lifetime.

More specifically, this invention relates to a process for producing an alkenyl-substituted aromatic compound which comprises catalytically reacting an alkyl-substituted aromatic compound in the vapor phase in the presence of molecular oxygen and a catalyst composed of palladium metal and a metal halide supported on an alumina carrier to convert it to the corresponding alkenyl-substituted aromatic compound, wherein said reaction is carried out in the presence of a catalyst composed of palladium metal and a metal halide supported on a carrier consisting substantially of α-alumina, said catalyst optionally containing a promoter ingredient selected from the group consisting of elements of Groups Ia, IIa, IIb and VIa of the periodic table and elements of Group VIII of the periodic table except palladium; and a catalyst suitable for use in the aforementioned process.

Typical known methods for producing alkenyl-substituted aromatic compounds such as styrene by catalytically reacting the corresponding alkyl-substituted aromatic compounds such as ethylbenzene are two types of vapor-phase catalytic reactions (1) and (2) schematically shown below.

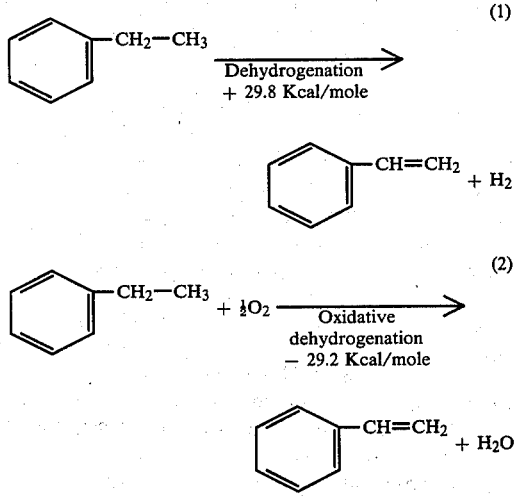

The catalytic dehydrogenating reaction represented by formula (1) is an endothermic reaction which has the disadvantage of requiring large quantities of a diluent and a reaction heat supplying medium such as high temperature steam. The progress of this catalytic dehydrogenation reaction is restricted in chemical equilibrium, and in order to achieve a commercially feasible ethylbenzene conversion, the partial pressure of ethylbenzene, the reaction temperature and other reaction conditions are considerably restricted. This method is also disadvantageous in the selection and control of the reaction conditions.

In contrast, the catalytic oxidative dehydrogenation represented by formula (2) is an exothermic reaction, and in principle does not require the use of high-temperature steam as a diluent and a reaction heat supplying medium. It also has the advantage that the chemical equilibrium is extremely deviated to the styrene side.

The process of this invention relates to the catalytic oxidative dehydrogenation reaction which can be expressed by formula (2). This type of reaction, however, has the disadvantage that the reaction is carried out in the presence of molecular oxygen, and tends to involve undesirable side-reactions such as a combustion reaction or a reaction of forming oxygen-containing compounds. It has been desired therefore to develop a catalyst which maintains a high selectivity and a long active lifetime while bringing about a high conversion of ethylbenzene.

It is known to perform a vapor-phase oxidative dehydrogenation reaction at a temperature of 50° to 350° C. by using a catalyst obtained by supporting a metal of the platinum group including palladium metal on a carrier having a surface area of more than 10 m$^2$/g (Japanese Patent Publication No. 3322/69 published on Feb. 12, 1969, corresponding to British Patent Specification No. 1,098,697 published on Jan. 16, 1968). This Publication discloses the use of γ-alumina (available under the tradename "Alcoa" type F10) as a carrier. The alumina-supported palladium metal catalyst disclosed in this patent has the defect that it has low catalytic activity, and when the reaction is performed at a high temperature in order to increase the rate of the reaction, violent undesirable side-reactions such as a reaction of forming oxygen-containing compounds and a combustion reaction occur.

In an attempt to remove this defect, it was suggested to perform the aforesaid catalytic oxidative dehydrogenation reaction for producing styrene from ethylbenzene in the presence of a catalyst composed of palladium metal and a metal salt containing at least one halogen atom selected from the group consisting of chlorine, bromine and iodine which are supported on a carrier (Japanese Laid-Open Patent Publication No. 53333/75 published on May 12, 1975). This Publication exemplifies alumina as the carrier, and only γ-alumina is disclosed as the alumina. In a working example which gave the best result in this Publication, styrene was obtained in a one-pass yield of 44.1 mole % by reacting ethylbenzene at 300° C. in the presence of a catalyst composed of palladium metal and copper bromide supported on a γ-alumina carrier, and the amount of by-product $CO_2$ was only 3.3 mole. This yield is higher than the yields obtained with the use of palladium catalysts disclosed prior to this Publication. It has been found however that for commercial scale operation, this process still has problems to be solved.

The investigations by the present invention show that in the process suggested by Japanese Laid-Open Patent Publication No. 53333/75 in which styrene is produced by oxidative dehydrogenation of ethylbenzene in the presence of molecular oxygen and in the presence of the improved catalyst composed of palladium metal and a metal halogen compound supported on a γ-alumina carrier, a carbonaceous by-product deposits on the catalyst in an amount of as large as 10 to 50% by weight based on the weight of the catalyst before use after using the catalyst for several hours to several hundred hours, and the deposition of the carbonaceous by-product markedly hampers the catalytic activity of the catalyst. This by-product is presumably a styrene polymer which burns at about 400° to 500° C. in the presence of molecular oxygen. It was found that the palladium catalyst used in this Publication which is modified with a metal halogen compound gradually loses its halogen ingredient during the reaction, and its improving effect by the metal halogen compound is reduced, and that after a lapse of several hours to about sixty hours, the intended oxidative dehydrogenation reaction is inhibited, and an undesirable combustion reaction is promoted.

On further investigation in an attempt to remove the aforesaid defect, the present inventors unexpectedly found that the use of a γ-alumina carrier having a high specific surface area which is used commonly in the palladium catalyst and the catalyst composed of palladium metal and a metal halide in the above-cited prior Patent Publications is a serious cause of the aforesaid defects, and that the use of a carrier composed substantially of α-alumina as shown by X-ray diffraction can remove the above defects. It is the general common knowledge in the field of catalyst chemistry that a carrier having a high specific surface area is used for noble metal catalysts in order to increase the efficiency of using the noble metals and maintain them in the most highly dispersed state at the carrier surface. In fact, γ-alumina is used commonly in the above-cited prior suggestions. Accordingly, the outstanding improvement achieved by the use of α-alumina which goes away from the technical common knowledge is an unexpected surprising result.

On further investigation, it was found that favorable results can be obtained when the α-alumina has a pore volume ratio (Vmin), expressed by the following equation, of not more than about 0.2, preferably not more than about 0.15.

$$V\text{min} = V_A/(V_A + V_B)$$

wherein $V_A$ is the volume (ml/g) of pores which require a penetration pressure of 6,000 psi to 60,000 psi by the mercury penetration method, and $V_B$ is the volume (ml/g) of pores which require a penetration pressure of 900 psi to less than 6,000 psi.

It was also found that more favorable results can be obtained when the crystal size of supported palladium metal is about 200 Å to 600 Å. In view of the fact that the γ-alumina carrier used in the prior suggestions consists substantially of pores having a penetration pressure, as measured by the mercury penetration method, of 6,000 psi or more, and the heretofore suggested palladium metal supported on a γ-alumina carrier does not show the abovespecified crystal size, the oxidative dehydrogenation catalyst of this invention is a new type of catalyst which can be completely distinguished from the heretofore known catalysts.

Furthermore, it was found that the catalyst of this invention exhibits better catalytic performance when it contains a promoter ingredient selected from the group consisting of elements of Groups Ia, IIa, IIb and VIa of the periodic table, and elements of Group VIII of the periodic table other than palladium.

Thus, the present inventors found that the use of a palladium-type catalyst supported on a carrier consisting substantially of α-alumina contrary to the technical knowledge in the technical field of palladium-type catalysts supported on an aluminum carrier can eliminate the technical defects in the prior suggestions.

It is an object of this invention to provide a process for producing an alkenyl-substituted aromatic compound which comprises oxidatively dehydrogenating the corresponding alkyl-substituted aromatic compound in the vapor phase in the presence of a specified catalyst stably for long periods of time with superior catalytic activity and a high selectivity while advantageously inhibiting the occurrence of undesirable side-reactions.

Another object of this invention is to provide a palladium-type oxidative dehydrogenation catalyst which is especially useful for the production of alkenyl-substituted aromatic compounds.

According to the process of this invention, alkenyl-substituted aromatic compounds can be produced with commercial advantage by oxidatively dehydrogenating the corresponding alkyl-substituted aromatic compounds in the vapor phase in the presence of molecular oxygen and a catalyst composed of palladium metal and a metal halide which are supported on a carrier consisting substantially of α-alumina as determined by X-ray diffraction.

It is desirable that the carrier consisting substantially of α-alumina as determined by X-ray diffraction have a pore volume ratio (Vmin), defined hereinabove, of not more than about 0.2, preferably not more than about 0.15, and more preferably not more than about 0.07. $V_A$ and $V_B$ are the pore volume (ml/g) measured by the mercury penetration method using Porosimeter 60,000 psi, No. 5-7125A (33690-2) (made by American Instrument Co., Inc.). The measurement may be made at any desired point because the values measured, before supporting the catalyst ingredients, after the supporting and before the use of the catalyst, and after the supporting and after the use of the catalyst are substantially the same. In the present invention, the pore volume of the carrier is usually measured after the supporting of the catalyst ingredients and before or after the use of the catalyst in the reaction.

The pore volume ratio (Vmin) of a carrier consisting substantially of γ-alumina or a carrier composed of δ- or θ-alumina, as determined by the mercury penetration method, is about 1. In other words, the alumina carriers of the above types contain substantially only those pores which have a penetration pressure of 6,000 psi or higher. On the other hand, it was confirmed by the investigation of the present inventors that a carrier consisting of α-alumina contains pores having a pore size distribution in the region of a penetration pressure of 900 to less than 6,000 psi by the mercury penetration method, and contains only a trace of pores having a penetration pressure of at least 6,000 psi, and it also contains a considerable proportion of macropores having a penetration pressure of less than 900 psi which will be completely destroyed when the carrier is pulverized to a size smaller than 200 mesh (Tyler mesh; all mesh sizes in the present application are Tyler's mesh sizes). Hence, if the carrier consists only of α-alumina, its pore volume ratio (Vmin) is about 0. That the carrier consisting of α-alumina in accordance with this invention preferably has a Vmin of not more than about 0.2 means that it does not have to consist solely of α-alumina and may be one which consists substantially of α-alumina.

The investigations of the present inventors led to the confirmation that the pore volume ratio (Vmin) has to do with the content of α-alumina. Alumina having a Vmin of about 0.2 has an α-alumina content of at least about 80% based on the weight of the alumina. Alumina having a Vmin of about 0.15 has an α-alumina content of about 85% based on the weight of the alumina. Accordingly, in terms of the content of α-alumina instead of Vmin, carriers having an α-alumina content of at least 80% are preferred in this invention. More preferably, such carriers have an α-alumina content of at least about 85%, especially at least about 90%.

The α-alumina content of an alumina carrier can be measured as follows:

Five grams of an accurately weighed sample is placed in a vessel made of tungsten carbide, and pulverized for 5 minutes by a vibratory mill. The pulverized sample is filled in a holder made of punched aluminum, and its X-ray diffraction intensity is measured.

The standard sample used is α-$Al_2O_3$ (Vmin=0.00) obtained by calcining γ-$Al_2O_3$ (B-19, a product of Fujimi Kenmazai Kabushiki Kaisha; particle diameter 1.5 mm) in a muffle furnace at 1200° C. for 4 hours.

Using mixed samples having various mixing ratios (by weight) between the standard sample and γ-$Al_2O_3$, the diffraction intensity (half value width multiplied by the peak height) of the 113 plane (2θ=43.4°) of α-$Al_2O_3$ was measured under the following conditions by the same device as used to measure the particle diameter of palladium.

Target: Cu
Filter: Ni
Tube voltage: 40 KV
Tube current: 20 mA
Count full scale: 2000 c/sec.
Time constant: 1 second
Scanning speed: 0.25°/min
Recorder chart speed: 2 cm/min.
Divergency: 1°
Receiving slit: 0.15 mm/min.
Soller slit: 1°
Scatter slit: 1°

If the Vmin of the carrier consisting substantially of α-alumina as used in this invention exceeds about 0.2, the amount of a carbonaceous by-product deposited on the catalyst as a result of a side-reaction tends to increase, and therefore, the Vmin of the carrier is preferably not more than about 0.2. For example, in the case of a prior method in which a γ-alumina carrier having a Vmin of about 1 is used, a fairly large amount of a carbonaceous by-product deposits within a very short period of time, and the reaction cannot be carried out stably over long periods of time with superior activity and selectivity.

Furthermore, it is preferred that the crystal size of palladium metal supported on the carrier consisting substantially of α-alumina in its X-ray diffraction, should be about 200 to about 600 Å, more preferably about 300 to about 550 Å, and especially about 400 to about 500 Å.

The crystal size of palladium is measured in the following manner after the supported catalyst is pulverized to a size smaller than 200 mesh before or after use in the reaction.

The diffraction lines of the sample are examined using a Geigerflex (a totally automatic remote control type, a product of Rigaku Denki Kabushiki Kaisha) under the following measuring conditions.

Target: Cu
Filter: Ni
Voltage: 40 KVP
Current: 30 mA
Count full scale: 2000 to 4000 c/sec.
Time constant: 1 second
Scanning speed: 0.25°/min.
Recorder chart speed: 2 cm/min.
Divergency: 1°
Receiving slit: 0.3 mm
Sollar slit: 1°

In accordance with ASTM Card No. 5-0681, the diffraction pattern based on the above examination at an interplanar spacing d=2.246 Å (111 plane, 2θ=40.11°) is recorded, and the half value width of the sample is measured. The crystal size (Å) of palladium, which is represented by t, is calculated by using the half value width in accordance with the following equation (3-13)

$$B=0.9\lambda/t.\cos\theta \qquad (3\text{-}13)$$

wherein
$\lambda=1.5405$ Å (a constant of Cu-K$\alpha_1$)
$\cos\theta=0.76604$
B=the half value width converted to a radian unit, which is described at page 262 of B. D. Cullity, "ELEMENTS OF X-RAY DIFFRACTION", published by Addison-Wesley Publishing Co., Inc. (1967).

As stated above, it was the technical common knowledge that in the case of a noble metal catalyst such as a palladium catalyst, a carrier having a high surface area capable of maintaining the noble metal in the highly dispersed state on the surface of the carrier is used so as to increase its efficiency of utilization, and the use of the catalyst at high temperatures is avoided to prevent a reduction in catalytic activity. In the present invention, however, the use of a carrier consisting substantially of α-alumina preferably having a Vmin of not more than about 0.2 with the palladium metal supported on the carrier preferably having a crystal size of at least about 200 Å and especially at least about 300 Å contrary to the technical common knowledge can permit the catalytic oxidative dehydrogenation reaction with superior high selectivity over a long period of time.

Depending upon the conditions for modifying with a metal halide, palladium is sometimes present on the carrier as palladium oxide or $K_2PdBr_4$ after supporting on the carrier and before use in the reaction. In such a case, the crystal size of palladium may be determined after the catalyst has been used in the reaction or exposed to conditions same as the reaction conditions. The same holds true in the case of using a promotor.

In a preferred embodiment of the present invention, there is no substantially great difference in selectivity between a catalyst having a palladium crystal size of less than 200 Å and a catalyst having a palladium crystal size of at least 200 Å before the catalyst attains the steady state in the early stage of reaction. In the steadily active state, the catalyst having a palladium crystal size of at least 200 Å can maintain a selectivity of as high as at least about 90%, for example about 95 to 97%, in the oxidative dehydrogenation of ethylbenzene to styrene, whereas the catalyst having a palladium crystal size of less than 200 Å gives a selectivity of about 80%. Hence, the use of catalysts having a palladium crystal size of at least 200 Å is preferred.

The alumina carrier used in this invention which consists substantially of α-alumina in its X-ray diffraction, and preferably has a pore volume ratio (Vmin) of not more than about 0.2 may be commercially available grades of α-alumina or α-alumina obtained by heat-treating γ-alumina, δ-alumina or θ-alumina by known procedures. Conversion to α-alumina by heat-treatment can be performed at any desired stage of catalyst preparation before supporting the metal halide compound.

For example, γ-, δ- or θ-alumina may be heated to a temperature of about 1100° to about 1300° C. Or a palladium compound is impregnated in or adsorbed to alumina, and then the alumina is heated to the above temperature. Or after the supporting, the palladium compound is reduced with hydrogen to palladium metal, and then the catalyst is heated to the above temperature. Another method is to heat-treat such a reduction product further in the air, and then heat-treat it to the above temperature thereby to convert the carrier alumina substantially to α-alumina. Still another method is to heat-treat γ-alumina to about 1000° C. to convert it to δ- or θ-alumina, deposit a palladium compound, and then heat-treat the supported catalyst to about 1100° C. to about 1300° C. to convert it to α-alumina. It is also possible to heat-treat a kneaded mixture of a palladium compound and an alumina sol, or a co-precipitate from an aqueous solution of a palladium compound and an aluminum compound to convert it substantially to α-alumina.

The carrier used in this invention which consists substantially of α-alumina in its X-ray diffraction may contain very small amounts of other metal compounds, for example, up to about 0.01%, based on the weight of the carrier, of a metal oxide such as $Fe_2O_3$, $CaO$, $Na_2O$, $K_2O$ or $MgO$ and up to about 0.1% of $SiO_2$.

The crystal size of palladium can be adjusted by various means. For example, a palladium compound such as palladium chloride or palladium oxide or metal palladium supported on a carrier consisting substantially of α-alumina is calcined at a temperature of about 700° to 1300° C., preferably about 800° to 1200° C., more preferably about 900° to 1100° C., thereby to adjust the palladium crystal size to at least about 200 Å. The crystal size of palladium can also be adjusted by performing the above heat treatment without prior reduction with hydrogen. Furthermore, the crystal size adjustment can be performed by calcining a composition obtained by supporting a palladium compound such as palladium chloride on an alumina carrier of the γ-, δ- or θ-type, a composition obtained by reducing the above composition with hydrogen, or a composition obtained by heat-treating the hydrogen-reduced composition at a temperature of about 200° to about 1000° C. in the air, at a temperature of about 1100° to 1300° C. at which temperature the alumina can be converted substantially to α-alumina. Desirably, the catalyst of this invention should have a specific surface area, measured by the BET method, of at least about 2 m²/g, preferably at least about 5 m²/g, more preferably at least about 10 m²/g. Calcination temperatures exceeding about 1300° C. cause the reduction of the specific surface area of the carrier, and therefore, the calcination temperature should preferably be not more than about 1300° C.

The deposition of a palladium compound on the carrier can be performed by kneading an alumina sol and a palladium compound, or by forming a coprecipitate from an aqueous solution containing an aluminum compound such as aluminum nitrate, aluminum chloride or aluminum acetate and an aqueous solution of a palladium compound; or by impregnating a palladium compound in the carrier or causing its adsorption to the carrier. In the kneading method or the coprecipitation method, the proportion of palladium deposited on the carrier can be changed as needed. For example, about 0.1 to about 100 parts by weight, preferably about 0.1 to about 50 parts by weight, more preferably, about 0.5 to 20 parts by weight, per 100 parts by weight of the carrier, of palladium metal can be deposited on the carrier. In the impregnating or adsorbing method, the suitable amount of palladium metal deposited on the carrier is about 0.1 to about 10 parts by weight, preferably about 0.1 to about 5 parts by weight, per 100 parts by weight of the carrier.

Specific examples of the palladium compound are palladium chloride, a palladium nitrate or palladium sulfate, and the use of palladium chloride is especially preferred.

The supporting or depositing means are well known. For example, in the kneading method, a powder or aqueous solution of palladium chloride is added to commercially available alumina sol containing 10 to 30% by weight of alumina, and they are kneaded for several hours by a kneader; the mixture is dried using a hot water bath to an extent suitable for extrusion molding, it is molded by an extrusion molding machine having an extrusion orifice with a diameter of 1 to 20 mm; the molded mixture is cut to a suitable length, dried, and reduced with hydrogen; the alumina is converted substantially to α-type at a temperature of at least 1100° C.; and the catalyst is further modified with a metal halide. The impregnating method may be performed by dipping α-alumina in an aqueous solution of palladium chloride, withdrawing it after a lapse of a suitable period of time, and drying it. When it is desired to deposit a large quantity of palladium, the impregnated carrier is evaporated to dryness under reduced pressure to deposit palladium chloride forcibly, followed by hydrogen reduction or high-temperature treatment and by modification with a metal halide. When alumina having a high specific surface area, such as γ-, δ- or θ-alumina is used, about 2% by weight of palladium chloride is completely adsorbed. Hence, in this case, the supernatant liquid is removed by filtration, and the solid is washed with pure water and dried. Then, chlorine was removed by hydrogen reduction, and the product is heat-treated at temperatures and for periods sufficient for conversion of α-alumina, followed by modification with a metal halide. Reduction of the deposited palladium compound to palladium metal can be performed, for example, by heating at about 100° to about 800° C. in an atmosphere of hydrogen.

The catalyst of this invention consists of a carrier consisting substantially of α-alumina in its X-ray diffraction, preferably having a pore volume ratio (Vmin) of not more than about 0.2, more preferably not more than about 0.15, and palladium metal preferably having a crystal size of about 200 to 600 Å and a metal halide which are supported on the carrier.

Metal bromides are especially preferred as the metal halide. The use of bromides of metals of Groups I and II of the periodic table is preferred. Examples of the metal bromide compounds are potassium bromide, sodium bromide, cesium bromide, rubidium bromide, magnesium bromide, calcium bromide, copper bromide, silver bromide, zinc bromide, and mercury bromide. If desired, compounds of halogens other than fluorine can also be used. Among these, potassium bromide and sodium bromide are especially preferred. Desirably, the deposition of such a metal halide on the carrier is performed after depositing palladium metal. This can be accomplished, for example, by impregnating α-alumina having palladium metal deposited thereon with an aqueous solution of the water-soluble metal bromide compound, and then drying it. It is desirable to perform the drying at a temperature of 110° C. or higher. In order to increase the initial activity of the catalyst, the catalyst may be heat-treated in an atmosphere of air. The heating treatment is carried out at about 200° to 450° C., preferably at about 250° to 400° C., for about 2 to 20 hours.

The amount of the metal halide compound used is preferably about 0.1 to about 20, more preferably about 0.25 to about 10, especially preferably about 0.5 to about 5, as a molar ratio to palladium metal.

The catalyst in accordance with this invention may contain a promotor which is an element of Group Ia of the periodic table, an element of Group IIa of the periodic table, an element of Group IIb of the periodic table, an element of Group VIa of the periodic table, an element of Group VIII of the periodic table other than palladium, or a mixture of at least two of these elements. The use of the promotor ingredient makes it possible to obtain a high ethylbenzene conversion easily. With a catalyst containing palladium metal alone, when the one-pass conversion of ethylbenzene is elevated at least to 50 mole%, the styrene selectivity tends to decrease. The use of a promotor ingredient makes it possible to achieve both an ethylbenzene conversion of at least 50 mole% and a styrene selectivity of at least 80 mole%, in a preferred example at least 90 mole%, and in a more preferred example at least 95 mole%. Furthermore, the use of the promotor metal markedly increases the activity of palladium metal, and relatively decreases the importance of the catalyst surface area. As a result of the aforesaid promoting effect, Vmin can be reduced almost to zero, and it is possible to prepare a highly stable and reproducible catalyst substantially free from the deposition of a carbonaceous by-product or the formation of undesirable oxygen-containing compounds.

Examples of preferred elements used as the promotor ingredient are elements of Group Ia of the periodic table selected from Li, Na, K, Rb and Cs; elements of Group IIa of the periodic table selected from Be, Mg, Ca, Sr, Ba and Ra; elements of Group IIb of the periodic table selected from Zn and Cd; elements of Groups VIa of the periodic table selected from Cr, Mo, W and U; and elements of Group VIII of the periodic table selected from Fe, Co, Ni, Ru, Rh, Os, Ir and Pt.

Examples of the use of two or more promotor ingredients are combinations of at least one element selected from the group consisting of elements of Group IIa of the periodic table, elements of Group VIa and elements of Group VIII other than Pd with at least one element selected from the group consisting of elements of Group IIa which are different from those selected above, elements of Group IIa which are different from those selected above, elements of Group VIa which are different from those selected above, and elements of Group VIII other than Pd which are different from those selected above. Preferred examples are combinations of elements of group IIb, especially Zn and Cd with at least one element selected from the group consisting of elements of Group Ia, elements of Group IIa, elements of Group VIa and elements of Group VIII other than Pd.

The promotor ingredient can be incorporated in the catalyst by the following procedure.

The most preferred method for depositing the promotor ingredient comprises dipping $\gamma$-$Al_2O_3$ in a homogeneous aqueous solution of palladium chloride or palladium nitrate, especially palladium chloride, and a metal chloride or nitrate, subjecting the product to evaporation to dryness, drying and reduction with hydrogen by the procedure described hereinabove, and calcining the product under conditions which will convert it to α-alumina having the specified Vmin values. This may be followed by supporting a metal halogen compound and activating it by the method described hereinabove to prepare the catalyst of this invention.

Alternatively, a method may be used which comprises first calcining α-alumina having the specified Vmin values at about 1100° C., dipping the calcined product in the aforesaid homogeneous aqueous solution of the promotor ingredient, subjecting it to reduction with hydrogen, and then further calcining the product at 800° to 1300° C.

When a catalyst is to be prepared by the kneading method, it is desirable to knead a palladium compound and a compound of the promotor element with an alumina sol at the same time. On the other hand, when such a compound as ammonium paratungstate or ammonium paramolybdate is to be deposited by the impregnation method, a suitable method is to support the above compound on γ- or α-alumina, treat it in a muffle furnace at 300° to 500° C. to decompose the salt, and then to impregnate it with palladium chloride or palladium nitrate and a compound of the promotor element stable in an acidic aqueous solution.

The catalyst may also be prepared by first preparing a composition of palladium and aluminum, then depositing a compound of a promotor element, subjecting the composition to reduction with hydrogen, and then supporting a metal halogen compound with or without prior calcination treatment at 800° to 1300° C.

Examples of the compounds used as promotor ingredients include anhydrous lithium chloride (LiCl), lithium bromide ($LiBr.H_2O$), lithium carbonate ($Li_2CO_3$), lithium nitrate ($LiNO_3$), lithium oxalate ($Li_2C_2O_4$), lithium hydroxide ($LiOH.H_2O$), sodium chloride (NaCl), sodium bromide (NaBr), sodium carbonate ($Na_2CO_3.H_2O$), sodium citrate ($Na_3C_6H_5O_7.2H_2O$), sodium hydroxide (NaOH), sodium formate (HCOONa), sodium iodide (NaI), sodium lactate [$CH_3CH(OH)COONa$], sodium nitrate ($NaNO_3$), sodium oxalate ($Na_2C_2O_4$), calcium chloride ($CaCl_2$), calcium bromide ($CaBr_2.3H_2O$), calcium nitrate [$Ca(NO_3)_2.4H_2O$], calcium iodide ($CaI_2.6H_2O$), potassium nitrate ($KNO_3$), potassium chloride (KCl), potassium bromide (KBr), potassium hydroxide (KOH), potassium iodide (KI), rubidium chloride (RbCl), rubidium bromide (RbBr), rubidium nitrate ($RbNO_3$), cesium nitrate ($CaNO_3$), cesium chloride (CsCl), cesium bromide (CsBr), cesium iodide (CsI), cesium carbonate ($Cs_2CO_3.2H_2O$), beryllium nitrate solution [$Be(NO_3)_2$], magnesium chloride ($MgCl_2.6H_2O$), magnesium bromide ($MgBr_2.6H_2O$), magnesium hydroxide [$Mg(OH)_2$], magnesium nitrate

[Mg(NO$_3$)$_2$.6H$_2$O], strontium chloride (SrCl$_2$.6H$_2$O; SrCl$_2$), strontium hydroxide [Sr(OH)$_2$.8H$_2$O], strontium iodide (SrI$_2$.6H$_2$O), strontium nitrate [Sr(NO$_3$)$_2$], barium chloride (BaCl$_2$; BaCl$_2$.2H$_2$O), barium nitrate [Ba(NO$_3$)$_2$], barium iodide (BaI$_2$.2H$_2$O), barium oxalate (BaC$_2$O$_4$.H$_2$O), barium acetate [Ba(CH$_3$COO)$_2$], barium carbonate (BaCO$_3$), radium chloride (RaCl$_2$), chromium chloride (CrCl$_3$.6H$_2$O), chromium nitrate [Cr(NO$_3$)$_3$.9H$_2$O], chromium trioxide (CrO$_3$), molybdic acid (H$_2$MoO$_4$.H$_2$O), molybdic anhydride (MoO$_3$), molybdenum chloride (MoCl$_5$), ammonium molybdate [(NH$_4$)$_6$Mo$_7$O$_{24}$.4H$_2$O], tungstic acid (H$_2$WO$_4$), ammonium paratungstate [5(NH$_4$)$_2$O.12WO$_3$.5H$_2$O], uranyl acetate [UO$_2$(CH$_3$COO)$_2$.2H$_2$O], uranyl nitrate [UO$_2$(NO$_3$)$_2$.6H$_2$0], ferric chloride (FeCl$_3$.6H$_2$O; FeCl$_3$), ferric hydroxide [Fe(OH)$_3$], ferric nitrate [Fe(NO$_3$)$_3$.9H$_2$O], ferrous oxalate (FeC$_2$O$_4$.2H$_2$O), ferrous lactate [Fe(CH$_3$CHOHCOO)$_2$.3H$_2$O], cobalt chloride (CoCl$_2$.6H$_2$O; CoCl$_2$), cobalt nitrate [Co(NO$_3$)$_2$.6H$_2$O], cobalt bromide (CoBr$_2$.6H$_2$O), cobalt acetate [Co(CH$_3$COO)$_2$.4H$_2$O], nichel chloride (NiCl$_2$.6H$_2$O; NiCl$_2$), nickel nitrate [Ni(NO$_3$)$_2$.6H$_2$O], nickel acetate [Ni(CH$_3$COO)$_2$.4H$_2$O], nickel formate [Ni(HCOO)$_2$.2H$_2$O], ruthenium chloride (RuCl$_4$.5H$_2$O), ruthenium nitrate [Ru(NO$_3$)$_3$.6H$_2$O], rhodium chloride (RhCl$_3$; RhCl$_3$.4H$_2$O), rhodium nitrate [Rh(NO$_3$)$_3$.6H$_2$O], osmium chloride (OsCl$_3$), iridium chloride (IrCl$_4$), iridium bromide (IrBr$_3$.4H$_2$O; IrBr$_4$), chloroplatinic acid (H$_2$PtCl$_6$.6H$_2$O), ammonium chloroplatinic acid [(NH$_4$)$_2$PtCl$_6$.6H$_2$O], platinum chloride (PtCl$_4$.8H$_2$O), zinc acetate [Zn(CH$_3$COO)$_2$.2H$_2$O], zinc bromide (ZnBr$_2$), zinc nitrate [Zn(NO$_3$)$_2$.6H$_2$O], zinc iodide (ZnI$_2$), zinc lactate [Zn(C$_3$H$_5$O$_3$)$_2$.3H$_2$O], cadmium chloride (CdCl$_2$.½H$_2$O; CdCl$_2$), cadmium bromide (CdBr$_2$.4H$_2$O), cadmium iodide (CdI$_2$), cadmium carbonate (CdCO$_3$), cadmium acetate [Cd(CH$_3$COO)$_2$.2H$_2$O], cadmium formate [Cd(HCOO)$_2$.2H$_2$O], and cadmium nitrate [Ca(NO$_3$)$_2$.4H$_2$O].

The amount of the promotor ingredient used can be varied properly. For example, it can be used in an amount of about 0.0001 to about 100, preferably about 0.001 to about 10, more preferably about 0.001 to about 5, in terms of an atomic ratio to Pd supported on alumina (moles of the promotor element/moles of Pd).

The catalyst of this invention may have any desired form such as a molded article or a powder. The molded article may be finely divided and re-molded prior to use.

According to the present invention alkenyl-substituted aromatic compounds are produced by reacting the corresponding alkyl-substituted aromatic compounds in the vapor phase in the presence of molecular oxygen and a catalyst composed of a carrier consisting substantially of α-alumina in its X-ray diffraction, preferably having a pore volume ratio (Vmin) of not more than about 0.2 and palladium metal preferably having a crystal size of about 200 to 600 Å. and a metal halide, preferably a metal bromide compound optionally with a promotor ingredient, which are deposited on the carrier.

Examples of the starting alkyl-substituted aromatic compounds are ethylbenzene, ethyltoluene, diethylbenzene, cumene, methyl isopropylbenzene, n-butylbenzene, tert-butylbenzene, methyl tert-butylbenzene, and ethyl-tert-butylbenzene. The process of this invention is especially suitable for the production of styrene from ethylbenzene. Hence, the process of the invention will be described below with reference to the production of styrene from ethylbenzene as an example.

The reaction may be performed at atmospheric pressure. If desired, elevated or reduced pressures may be employed. For example, pressures of about 0.1 kg/cm$^2$.G to about 20 kg/cm$^2$.G. The reaction temperature is about 150° to about 450° C., preferably about 200° to about 400° C., more preferably about 250° to about 350° C. At the above pressure and temperatures, ethylbenzene and molecular oxygen such as air are introduced into a reaction zone including the catalyst of this invention to bring them into contact with the catalyst. Preferably, the reaction should be carried out in the further presence of a compound of bromine and/or chlorine which is gaseous under the reaction conditions. Good results can also be obtained by performing the reaction in the copresence of steam. In a preferred embodiment of the process of this invention, ethylbenzene, molecular oxygen, steam and a compound of bromine and/or chlorine which is gaseous under the reaction conditions are introduced into the catalytic reaction zone to perform oxidative dehydrogenation of ethylbenzene. The molecular oxygen may be air, oxygen or a molecular-oxygen-containing gas obtained by diluting air or oxygen with an inert gas such as nitrogen or carbon dioxide. The inert gas may contain a small amount of carbon monoxide. The use of air is preferred in commercial operation. Furthermore, a suitable amount of an exhaust gas (consisting, for example, of oxygen, nitrogen, carbon dioxide and a small amount of carbon monoxide) from the reactor may be recycled to the reactor to reuse the unconverted oxygen and also to decrease the partial pressure of ethylbenzene in the raw materials. Examples of the compound of bromine and/or chlorine which is gaseous under the reaction conditions are inorganic compounds such as hydrogen bromide or hydrogen chloride, and bromine- and/or chlorine-substituted products of hydrocarbons containing 1 to 6 carbon atoms such as bromoform, bromoethane, propyl bromide, isopropyl bromide, chloroform, ethyl chloride, bromochloroethane, ethylene chloride, propyl chloride, isopropyl chloride, bromobenzene and chlorobenzene. Of these, hydrogen bromide, hydrogen chloride and bromoethane are preferred from the standpoint of their adding effects and costs. The use of hydrogen bromide is especially preferred.

In the reaction, the oxygen/ethylbenzene mole ratio is preferably about 1/10—about 5, more preferably about ¼—about 1. Steam is utilized preferably in a steam/ethylbenzene mole ratio of 0 to about 20, preferably about ½—about 10, more preferably about 1 to about 5.

The concentration of the bromine or chlorine compound in the gaseous mixture of the starting alkyl-substituted aromatic compound such as ethylbenzene and molecular oxygen is preferably less than 50 ppm, for example, about 0.1 to less than 50 ppm, preferably about 1 to about 30 ppm, especially preferably about 2 to about 20 ppm.

In the performance of the process of this invention, the presence of the above-specified small amounts of the bromine and/or chlorine compounds which are gaseous under the reaction conditions markedly helps to maintain the superior catalytic activity of the catalyst of this invention for long periods of time. For example, when the reaction in accordance with this invention is performed using the catalyst of this invention composed of palladium metal having a crystal size of about 200 Å or more and a metal bromide compound supported on a carrier consisting substantially of α-alumina in its X-ray diffraction in the copresence of about 2 to about 20 ppm of the bromine and/or chlorine compound, the excellent activity of the catalyst is stably retained over a long period of at least about 300 hours, frequently for more than 1000 hours, and styrene can be produced from ethylbenzene at a high styrene selectivity of about 90 to about 98%. Furthermore, the amount of bromine in the used catalyst is as high as about 92 to about 99% of that of the catalyst prior to use. In contrast, if the crystal size is less than 200 Å, the amount of bromine decreases to about 80% when the reaction is carried out under the same conditions. Thus, when the bromine and/or chlorine compound is used, the use of a catalyst having a palladium crystal size of at least about 200 Å is especially preferred. If the amount of the bromine and/or chlorine compound to be copresent in the reaction exceeds 50 ppm, the high selectivity of styrene can be maintained, but the ability of the catalyst to convert ethylbenzene is markedly reduced. This excessive amount is also undesirable because the increased amount of the bromine and/or chlorine compound added leads to an increase in the cost of auxiliary agents or to the possibility of corrosion of the equipment. In the present invention, the amount of the bromine and/or chlorine compound to be copresent may be very small, and the activity of the catalyst can be maintained stably for long periods of time without the corrosion of the equipment or the need to recover and re-utilize such a compound. It has been found that in the present invention, the above bromine and/or chlorine compound exhibits different behaviors from bromine and chlorine compounds used in the prior suggestions.

In the process of this invention, the catalyst can be used in any desired form such as in a fixed bed, a moving bed or a fluidized bed. In performing the process of this invention, the rate of feeding ethylbenzene is about 0.01 to about 1, preferably about 0.02 to about 0.5, mole/g-catalyst/hour. The time for contacting the starting gaseous mixture with the catalyst at the reaction temperature is about 0.1 to about 20 seconds, preferably about 0.2 to about 5 seconds. The gas space velocity (GHSV) may be about 100 to about 1000, preferably about 500 to about 5000, (STP-ml)/ml-catalyst/hour.

The diameter of the reaction tube, at the same GHSV, markedly affects the linear velocity of the starting gaseous mixture, and also affects the velocity of material diffusion on the catalyst surface and the velocity of material mixing in the reaction system. The form or size of the catalyst has similar effects, and so does the dilution of the catalyst by an inert substance. Accordingly, the ethylbenzene conversions described in the following examples for specifically illustrating the present invention are limited by the diameters of the reaction tubes and the forms and sizes of the catalysts given in the examples. They do not represent the maximum activities attainable by the catalysts of this invention, but they only represent relative evaluations of the catalysts tested. Accordingly, the present invention is not completely restricted by the ethylbenzene conversions given in the examples.

The catalysts of this invention may be used in any form of reaction such as the one in a fixed bed, a moving bed, or a fluidized bed.

The following Examples and Comparative Examples specifically illustrate the present invention. The analyses and determinations of the reaction products were all performed by gas chromatography. The ethylbenzene conversions, the styrene selectivities and the benzene ring decomposition ratios are defined by the following equations, and expressed in mole%.

$$\text{Ethylbenzene conversion} = \frac{[\text{recovered (styrene + toluene + benzene)} + \text{corrected* (carbon monoxide + carbon dioxide)}] \times 100}{[\text{recovered (ethylbenzene + toluene + benzene + styrene)} + \text{corrected (carbon monoxide + carbon dioxide)}]}$$

$$\text{Styrene selectivity} = \frac{\text{Recovered styrene} \times 100}{[\text{recovered (toluene + benzene + styrene)} + \text{corrected (carbon monoxide + carbon dioxide)}]}$$

$$\text{Benzene ring decomposition ratio} = \frac{\text{Corrected (carbon monoxide + carbon dioxide)} \times 100}{[\text{recovered (toluene + benzene + styrene)} + \text{corrected (carbon monoxide + carbon dioxide)}]}$$

*Corrected (carbon monoxide + carbon dioxide):
The value obtained by subtracting the amount in moles of carbon monoxide and carbon dioxide which are ascribable to the formation of benzene and toluene from the amount of these as formed, and dividing the resulting value by 8.

EXAMPLE 1

Alumina (100 parts by weight) obtained by calcining commercially available highly pure γ-alumina (spherical; diameter 1.5 mm; surface area by the BET method 180 m²/g) at 1000° C. for 4 hours in a muffle furnace was dipped in a 0.1 N hydrochloric acid solution of palladium chloride in an amount required for the alumina to support 2 parts by weight of palladium. Using a rotary evaporator, the impregnated alumina was dried under reduced pressure at 50° C., and further dried at 110° C.

The resulting composition was packed in a quartz reaction tube, and reduced in a stream of hydrogen at 500° C. for 4 hours. The hydrogen atmosphere was replaced by nitrogen, and then the reduced composition was heated in an atmosphere of air at 450° C. for 2 hours. The composition obtained was treated in a muffle surface at 1100° C. for 4 hours. The treated composition was impregnated with a 0.25 N potassium bromide solution containing potassium bromide in an equimolar amount to the supported palladium, and dried at 50° C. under reduced pressure by using a rotary evaporator, followed by drying at 110° C. for 24 hours in a dryer. The resulting composition was packed into a stainless steel tube, and calcined at 350° C. for 7 hours in a stream of air to afford a catalyst. This catalyst is expressed by the composition 1KBr-2Pd-100Al₂O₃. The alumina in the catalyst was mainly of α-type, and the crystal diameter of palladium was 450 Å. The Vmin of the catalyst was 0.123.

A stainless steel reaction tube having an inside diameter of 20 mm was packed with 20 ml of the catalyst and porcelain Raschig rings were filled above the catalyst layer to a height of 20 cm to provide a section for preheating the raw materials. The reaction tube was heated by a niter bath, and reaction was performed under the following conditions:

Steam/oxygen (fed as air)/ethylbenzene=2.8/0.43/1 (mole/mole)
Gas space velocity (GHSV)=725 (STP-ml raw material/ml-catalyst/hour)
Reaction temperature=285° C.
Hydrogen bromide concentration (HBr) in the raw material=5 ppm (by volume)

After 20 hours from the initiation of the reaction, the activity of the catalyst became stable. At the end of 200 hours after the beginning of the reaction, an ethylbenzene conversion of 42.9 mole%, a styrene selectivity of 97.6 mole%, and a benzene ring decomposition ratio of 1.8 mole% were obtained.

The catalyst was withdrawn, and the amount of a carbonaceous by-product which deposited on it was measured by a differential thermal gravimetric analysis method and found to be 0.45% by weight of the fresh catalyst.

EXAMPLE 2

Alumina (0.3 to 0.5 mm in particle diameter) having the same composition as in Example 1 was treated at 1100° C. for 6 hours to form a carrier. A catalyst having the composition 3KBr-2Pd-100Al$_2$O$_3$ was prepared under the same catalyst preparing conditions as in Example 1 except that the composition consisting of the alumina and palladium was heat-treated in a muffle furnace at 900° C. for 6 hours.

The same reaction tube as used in Example 1 was packed with 20 ml of the catalyst, and reaction was performed under the following conditions:
 Steam/oxygen (air)/ethylbenzene=3/0.6/1
 GHSV=850
 HBr=7 ppm
 Reaction temperature=288° C.

In 20 hours after the initiation of the reaction, the activity of the catalyst became steady. At the end of 1000 hours after the initiation of the reaction, an ethylbenzene conversion of 43.0 mole%, a styrene selectivity of 96.5 mole% and a benzene ring decomposition ratio of 3.0 mole% were obtained. The used catalyst contained a carbonaceous by-product deposited in an amount of 0.3% by weight. It had a Vmin of 0.066 and a palladium particle diameter of 399 Å. The alumina was mainly of α-type.

EXAMPLE 3

The same γ-alumina as used in Example 1 was calcined at 1100° C. for 6 hours in a muffle furnace. A catalyst having the composition 1KBr-2Pd-100Al$_2$O$_3$ was prepared under the same catalyst preparing conditions as in Example 1 except that the composition consisting of palladium and alumina was heat-treated in a muffle furnace at 900° C. for 6 hours.

The same reaction tube as used in Example 1 was packed with 20 ml of the catalyst, and it was used continuously for 360 hours under the reaction conditions summarized in Table 1. The performance of the catalyst at the end of 2 hours, 20 hours and 360 hours respectively was examined, and the results are shown in Table 1.

After use, the catalyst had a Vmin of 0.107 and a palladium crystal diameter of 432 Å, and the alumina was mainly of α-type. The amount of bromine supported was determined by a fluorescent X-ray method before and after use. Assuming that the amount of bromine supported before use was 1.0, its amount after use was 0.94.

EXAMPLES 4 AND 5

Calcination of alumina and impregnation of palladium chloride were performed using the same lot as in Example 3, and catalyst were prepared in the same way as in Example 3 except that the heat-treating temperature for the composition of palladium and alumina in the muffle furnace was changed to 1000° C. (Example 4) and 1200° C. (example 5). The two catalysts obtained had alumina mainly of α-type. The catalyst used in Example 4 had a Vmin of 0.118, while that used in Example 5 had a Vmin of 0.001. The performances of the catalyst were observed under the same conditions as in Example 3. The results obtained, the palladium crystal diameter and the amounts of supported bromine of the catalyst before and after use are summarized in Table 1.

COMPARATIVE EXAMPLE 1

Using a compound prepared in the same lot as in Example 3, a catalyst was prepared in the same way as in Example 3 except that the heat-treating temperature for the composition consisting of palladium and alumina in the muffle furnace was changed to 600° C. The catalyst contained mainly α-alumina and had a Vmin of 0.109. The performance of the catalyst was examined under the same conditions as in Example 3. The results obtained, the ratio of the amounts of bromine supported before and after use of the catalyst, and the palladium crystal diameter of the catalyst after use are given in Table 1.

COMPARATIVE EXAMPLE 2

The same γ-alumina having a particle diameter of 0.3 to 0.5 mm as used in Example 2 was dipped in a 0.1 N hydrochloric acid solution of palladium chloride. The impregnated alumina was evaporated to dryness, dried, reduced with hydrogen, and heated in the air under the same conditions as in Example 1. The treated alumina was then calcined at 1100° C. for 4 hours in a muffle furnace. Potassium bromide was supported in accordance with Example 1 to afford a catalyst having the composition 1KBr-2Pd-100Al$_2$O$_3$. Alumina of the catalyst was mainly of α-type. Its Vmin was 0.215, and the crystal diameter of palladium was 430 Å.

The same reaction tube as used in Example 1 was packed with 20 ml of the catalyst, and reaction was performed under the following conditions:
 Steam/oxygen (air)/ethylbenzene=4.8/0.47/1/0 (mole/mole)
 GHSV=1000
 HBr=10 ppm
 Reaction temperature=290° C.

At the end of 600 hours the initiation of the reaction, an ethylbenzene conversion of 35.3 mole%, a styrene selectivity of 94.7 mole% and a benzene ring decomposition ratio of 4.6 mole% were obtained. The amount of a carbonaceous by-product deposited on the withdrawn catalyst was 4.4% by weight.

COMPARATIVE EXAMPLE 3

CK-300 (a product of Ketjene Company) was dipped in a 0.1 N hydrochloric acid solution of palladium chloride, and allowed to stand for one day to cause the adsorption of palladium. The supernatant liquid was removed by suction filtration, and the palladium adsorbed (CK-300) was washed with pure water and dried at 110° C. for 24 hours. The resulting composition was reduced in a stream of hydrogen at 450° C. for 4 hours. The hydrogen atmosphere was replaced by nitrogen, and then the composition was treated in a stream of air at 350° C. for 2 hours. The resulting composition was dipped in a 0.25 N potassium bromide solution, dried under reduced pressure at 50° C. using a rotary evaporator, and further dried in a dryer at 110° C. for 24 hours. The composition 1KBr-2Pd-100Al$_2$O$_3$ was treated in a stream of air at 350° C. for 7 hours to form a catalyst.

The same reaction tube as used in Example 1 was packed with an intimate mixture of 20 ml of the catalyst and 20 ml of alumina (surface area 120 m$^2$/g) obtained by calcining CK-300 at 1000° C. for 4 hours in a muffle furnace. Reaction was performed under the following conditions:
Steam/oxygen (air)/ethylbenzene=5/0.5/1
HBr=5 ppm
GHSV=1000
Reaction temperature=250° C.

In 3.5 hours after the initiation of the reaction, an ethylbenzene conversion of 43.8 mole%, a styrene selectivity of 96.5 mole% and a benzene ring decomposition ratio of 0.8 mole% were obtained. At the end of 337 hours, an ethylbenzene conversion of 17.7 mole%, a styrene selectivity of 83.4 mole%, and a benzene ring decomposition ratio of 13.0 mole% were obtained. It was found that a carbonaceous by-product was deposited in an amount of 42.2% by weight on the withdrawn catalyst (the alumina was of o-type and had a Vmin of 0.966; the palladium crystal diameter was too small to permit detection of a peak at $2\theta=40.11°$) and 17.3% by weight on CK-300 treated at 1000° C. (the alumina was mainly of $\delta$ and $\theta$ types; Vmin 0.962). The amount of bromine deposited in the used catalyst was only 15% of that in the fresh catalyst.

COMPARATIVE EXAMPLE 4

Alumina (3 mm in diameter) having the same composition as in Example 1 was treated at 1000° C. for 4 hours, and using the treated alumina, a catalyst having the composition 1KBr-2Pd-100Al$_2$O$_3$ was prepared under the same conditions as in Comparative Example 1.

The same reaction tube as used in Example 1 was packed with 20 ml of the catalyst, and reaction was performed under the following conditions:
Steam/oxygen (air)/ethylbenzene=15.4/0.5/1
GHSV=1500
Reaction temperature=275° C.
HBr=5 ppm In 2 hours after the initiation of the reaction, an ethylbenzene conversion of 28.2 mole%, a styrene selectivity of 96.8 mole% and a benzene ring decomposition ratio of 0.7 mole% were obtained. At the end of 230 hours after the initiation of the reaction, an ethylbenzene conversion of 24.9 mole%, a styrene selectivity of 87.0 mole% and a benzene ring decomposition ratio of 9.8 mole% were obtained. The used catalyst contained $\delta$ and $\theta$ aluminas and had a Vmin of 0.999. The crystal diameter of palladium could not be measured. A carbonaceous by-product was seen to be deposited on the catalyst in an amount of 11.0% by weight.

EXAMPLE 6

A catalyst having the composition 2KBr-1Pd-100Al$_2$O$_3$ was prepared in the same way as in Example 1 except that the same $\gamma$-alumina as used in Example 1 was treated at 1100° C. for 6 hours in a muffle furnace. The catalyst mainly contained $\alpha$-type alumina and had a Vmin of 0.004 and a palladium crystal diameter of 330 Å.

A stainless steel reaction tube having an inside diameter of 15 mm was packed with 12.7 ml of the catalyst, and Raschig rings were filled above the catalyst layer to a height of 15 cm to provide a layer for preheating the raw materials. The reaction tube was heated with a niter bath, and reaction was performed under the following conditions:
Steam/oxygen (air)/ethylbenzene=5/0.5/1
GHSV=1000
Reaction temperature=285° C.
HBr=5 ppm The performance of the catalyst was examined at the end of 20 hours after the initiation of the reaction, and the results are shown in Table 2.

EXAMPLES 7 AND 8

Catalyst preparation and reaction were performed under the same conditions as in Example 6 except that the metal bromide used in Example 6 was changed to sodium bromide (Example 7) and to calcium bromide (Example 8). The performances of the catalysts at the end of 6 hours after the initiation of reaction were observed, and the results are shown in Table 2. The crystal type, Vmin and palladium crystal diameter of the catalyst were much the same as those in Example 6.

COMPARATIVE EXAMPLE 5

A catalyst having the composition 1KBr-2Pd-100Al$_2$O$_3$ was prepared by the same preparing method as in Example 6.

The same reaction tube as used in Example 1 was charged with 20 ml of the catalyst, and the reaction was performed under the following conditions:
Steam/oxygen (air)/ethylbenzene=5/0.5/1 (mole/mole)
GHSV=1000
Reaction temperature=300° C.

The performance of the catalyst was observed at the end of 3.5, 17, 33, and 100 hours after the initiation of the reaction, and the results are shown in Table 3.

EXAMPLE 9

Using a catalyst of the same lot as in Comparative Example 5, reaction was performed under the same way as in Comparative Example 5 except that ethyl bromide in a concentration of 5 ppm in the starting gaseous materials was added. The performance of the catalyst was observed, and the results obtained are shown in Table 3. The alumina in the used catalyst was substantially of $\alpha$-type, and had a Vmin of 0.011 and a palladium crystal diameter of 461 Å.

EXAMPLE 10

The same reaction tube as used in Example 1 was packed with 20 ml of a catalyst having the same composition as in Example 2 and prepared under the same conditions using the same carrier as in Example 3. Reaction was performed under the following conditions:
Steam/oxygen (fed as air)/ethylbenzene=3.1/0.52/1.0
GHSV=1030
HCl=10 ppm
Reaction temperature=288° C.

At the end of 288 hours after the initiation of the reaction, an ethylbenzene conversion of 35.2 mole%, a styrene selectivity of 95.2 mole% and a benzene ring decomposition ratio of 4.3 mole% were obtained. The used catalyst contained alumina which was substantially of $\alpha$-type, and had a Vmin of 0.075 and a palladium particle diameter of 379 Å. Assuming that the amount of bromine deposited in the catalyst before use was 1.0, the amount of bromine deposited in the withdrawn catalyst was 0.86 and chlorine was deposited in an amount corresponding to 0.12, as found by a fluorescent X-ray analysis method.

EXAMPLE 11

γ-alumina used in Example 2 was calcined at 1150° C. for 6 hours in a muffle furnace, and dipped in a 0.1 N hydrochloric acid solution of palladium chloride. It was dried by a rotary evaporator under reduced pressure, and dried further at 110° C. The product was packed into a quartz reaction tube, and reduced in a stream of hydrogen at 500° C. for 4 hours. Hydrogen was replaced by nitrogen, and the product was cooled to room temperature. The resulting composition was dipped in a 0.25 N aqueous solution of potassium bromide, and then treated by the same procedure as in Example 1 to afford a catalyst having the composition 3KBr-2Pd-100Al$_2$O$_3$. The alumina in the catalyst was substantially of α-type. It had a Vmin of 0.001 and a palladium crystal diameter of 372 Å.

The same reaction as used in Example 6 was packed with 12.7 ml of the catalyst, and reaction was performed under the following conditions:

Steam/oxygen (air)/ethylbenzene=5.6/0.52/1.0
GHSV=1070
HBr=5 ppm
Reaction temperature=285° C.

At the end of 483 hours, an ethylbenzene conversion of 37.0 mole%, a styrene selectivity of 95.7 mole% and a benzene ring decomposition ratio of 3.8 mole% were obtained.

COMPARATIVE EXAMPLE 6

The same reaction tube as used in Example 6 was packed with 12.7 ml of a catalyst of the same lot as the catalyst used in Example 5. Reaction was performed for 7 hours under the same reaction conditions as in Example 5 except that hydrogen bromide was not added. Then, the supply of steam was stopped, and the reaction was continued under the following conditions:

Oxygen (air) ethylbenzene=0.69/1 (mole/mole)
GHSV=520 (STP-ml starting materials/ml-catalyst/hour)
Reaction temperature=285° C.

At the end of 10.5 hours after the initiation of the reaction, an ethylbenzene conversion of 24.7 mole%, a styrene selectivity of 97.0 mole% and a benzene ring decomposition ratio of 1.0 mole% and a (benzene+toluene) selectivity of 2.0 mole% were obtained.

EXAMPLE 12

A catalyst having the composition 2KBr-2Pd-100Al$_2$O$_3$ was prepared in accordance with the same catalyst preparing method as in Example 1. The alumina in the catalyst was substantially of α-type, and it had a Vmin of 0.143 and a palladium crystal diameter of 434 Å. A stainless steel reaction tube having an inside diameter of 6 mm was packed with 12.7 ml of the catalyst, and sintered alumina having a particle size of 1 to 1.5 mm was filled above the catalyst layer to a height of 15 cm to provide a preheating section. Reaction was performed under the following conditions:

Steam/oxygen (air)/ethylbenzene=5/0.5/1
GHSV=1000
HBr=2 ppm
Reaction temperature=285° C.
Heated by a niter bath At the end of 1.5 hours after the initiation of the reaction, an ethylbenzene conversion of 37.0 mole%, a styrene selectivity of 97.7 mole% and a benzene ring decomposition ratio of 1.1 mole% were obtained.

EXAMPLE 13

A catalyst (12.7 ml) of the same lot as the catalyst used in Example 12 was mixed sufficiently with 33.3 ml of alumina obtained by calcining the same γ-alumina as used in Example 1 at 1300° C. for 5 hours. The mixture was packed into the same reaction tube as used in Example 6, and reaction was performed under the same reaction conditions as in Example 12. In 2 hours after the initiation of the reaction, an ethylbenzene conversion of 29.5 mole%, a styrene selectivity of 97.8 mole%, and a benzene ring decomposition ratio of 1.0 mole% were obtained.

EXAMPLE 14

The same reaction tube (inside diameter 15 mm) as used in Example 6 was packed with 12.7 ml of a catalyst from the same lot as the catalyst used in Example 12, and reaction was performed under the same reaction conditions as in Example 12. In 2 hours after the initiation of the reaction, an ethylbenzene conversion of 21.4 mole%, a styrene selectivity of 97.3 mole% and a benzene decomposition ratio of 1.1 mole% were obtained.

EXAMPLE 15

The same γ-alumina as used in Example 1 was treated in a muffle furnace at 1100° C. for 4 hours. Palladium chloride was deposited on the treated alumina, reduced with hydrogen, and heat-treated in a stream of air in the same way as in Example 1. The treated composition was calcined in a muffle furnace at 1100° C. for 6 hours to afford a catalyst having the composition 2KBr-2Pd-100Al$_2$O$_3$. The catalyst was pulverized and screened to a size of 100 to 150 mesh. The alumina in the catalyst was mainly of α-type, and it had a Vmin of 0.005 and a palladium crystal diameter of 470 Å.

A gas flow regulating section consisting of a layer of quartz fragments was provided at the lower portion of a quartz reaction tube with an inside diameter of 17 mm equipped with a raw material preheating tube and a thermocouple protecting tube with an outside diameter of 5 mm extending through the center of the reaction tube. The powdery catalyst (10 ml) was filled into the reaction tube, and reaction was performed in a fluidized bed under the following conditions:

Steam/oxygen (air)/ethylbenzene=5/0.5/1 (mole/mole)
GHSV=2000 (STP-ml starting materials/ml-catalyst/hour)
HBr=20 ppm
Reaction temperature=325° C. (heated in a cylindrical electric furnace)

In 10 hours after the initiation of the reaction, an ethylbenzene conversion of 25.7 mole%, a styrene selectivity of 96.9 mole%, a benzene ring decomposition ratio of 2.0 mole%, and a (benzene+toluene) selectivity of 1.1 mole% were obtained.

EXAMPLE 16

A catalyst from the same lot as the catalyst used in Example 15, without pulverization, was packed into the same reactor as used in Comparative Example 5 in an amount of 12.7 ml. The Vmin and palladium crystal diameter of the catalyst were the same as those of the pulverized catalyst. Reaction was performed under the following conditions:

- Steam/oxygen (air)/ethylbenzene = 4.7/0.44/1 (mole/mole)
- GHSV = 980 (STP-ml starting materials/ml-catalyst/hour)
- HBr = 5 ppm
- Reaction temperature = 275° C.

In 8 hours from the initiation of the reaction, an ethylbenzene conversion of 36.8 mole%, a styrene selectivity of 98.7 mole% and a benzene ring decomposition ratio of 0.4 mole% were obtained.

COMPARATIVE EXAMPLE 7

CK-300 (a product of Ketjene Company) was treated in a muffle furnace at 900° C. for 3 hours, and a catalyst having the composition 1KBr-1Pd-100Al$_2$O$_3$ was prepared by the same procedure and under the same conditions as in Comparative Example 3.

The same reactor as used in Example 6 was packed with 12.7 ml of the catalyst, and reaction was performed under the following conditions:
- Steam/oxygen (air)/ethylbenzene = 9.3/1/1
- GHSV = 2100

Reaction temperature = 250° C.

At the end of 35 hours after the initiation of the reaction, an ethylbenzene conversion of 36.7 mole%, a styrene selectivity of 95.8 mole%, and a benzene ring decomposition ratio of 1.9 mole% were obtained. At the end of 48 hours after the initiation of the reaction, an ethylbenzene conversion of 25.8 mole%, a styrene selectivity of 72.9 mole% and a benzene ring decomposition ratio of 22.3 mole% were obtained.

COMPARATIVE EXAMPLE 8

The same γ-alumina as used in Example 1 was treated by the same procedure as in Comparative Example 3 to afford a catalyst having the composition 1KBr-2Pd-100Al$_2$O$_3$. The same reaction tube as used in Example 6 was charged with 12.7 ml of the catalyst, and reaction was performed under the following conditions:
- Steam/oxygen (air)/ethylbenzene = 5/0.5/1
- GHSV = 1000
- Reaction temperature = 275° C.

In 4 hours after the initiation of the reaction, an ethylbenzene conversion of 52.1 mole%, a styrene selectivity of 94.2 mole%, and a benzene ring decomposition ratio of 1.9 mole% were obtained. At the end of 16 hours from the start of the reaction, an ethylbenzene conversion of 24.8 mole%, a styrene selectivity of 73.1 mole% and a benzene ring decomposition ratio of 14.3 mole% were obtained.

TABLE 1

|  |  | Comparative Example 1 | Example 3 | Example 4 | Example 5 |
|---|---|---|---|---|---|
| Catalyst composition |  |  | 1KBr-2Pd-100Al$_2$O$_3$ |  |  |
| Pd-Al$_2$O$_3$ calcining temperature | °C. | 600 | 900 | 1000 | 1200 |
| Reaction conditions H$_2$O/EB | mole/mole | 5.1 | 4.9 | 5.0 | 5.3 |
| O$_2$ (air)/EB | mole/mole | 0.5–0.6 | 0.47 | 0.5 | 0.58 |
| GHSV | C.C.-Starting materials/C.C.-catalyst/hr | 1000–1100 | 1050 | 1000 | 1100 |
| HBr | ppm/Starting mixture | 10 | 10 | 10 | 10 |
| Temperature | °C. | 288–290 | 291 | 285 | 290 |
| Ethylbenzene conversion (mole %) | at 3 hours | 18.0 | 37.1 | 24.9 | 12.4 |
|  | 20 hours | 38.4 | 44.5 | 36.4 | 19.4 |
|  | 360 hours | 36.1 | 44.8 | 38.8 | 23.9 |
| Styrene selectivity (mole %) | at 3 hours | 95.3 | 97.5 | 96.4 | 97.2 |
|  | 20 hours | 89.6 | 96.5 | 97.9 | 98.2 |
|  | 360 hours | 88.8 | 96.7 | 97.9 | 98.9 |
| Benzene ring decomposition ratio (mole %) | at 3 hours | 2.9 | 1.7 | 2.2 | 1.6 |
|  | 20 hours | 9.4 | 2.3 | 1.0 | 1.2 |
|  | 360 hours | 10.4 | 2.2 | 1.0 | 0.5 |
| (Benzene + toluene) selectivity (mole %) | at 3 hours | 1.8 | 0.8 | 1.3 | 1.2 |
|  | 20 hours | 1.0 | 1.2 | 1.1 | 0.6 |
|  | 360 hours | 0.8 | 1.1 | 1.1 | 0.6 |
| Ratio of bromine supported | (before use/after use) | 0.83 | 0.94 | 1.00 | 1.00 |
| V$_{min}$ |  | 0.109 | 0.107 | 0.118 | 0.001 |
| Palladium crystal diameter (Å) | Before use | — | 417 | 434 | 432 |
|  | After use | 150 | 432 | 458 | 422 |

TABLE 2

|  |  | Example 6 | Example 7 | Example 8 |
|---|---|---|---|---|
| Catalyst composition (omitting 100Al$_2$O$_3$) |  | 2KBr-1Pd | 2NaBr-1Pd | 2CaBr$_2$-1Pd |
| Ethylbenzene conversion | mole % | 37.1 | 28.7 | 19.7 |
| Styrene selectivity | mole % | 98.4 | 93.5 | 96.9 |
| Benzene ring decomposition ratio | mole % | 0.7 | 5.3 | 1.2 |
| (Benzene + toluene) selectivity | mole % | 0.9 | 1.2 | 0.9 |
| V$_{min}$ |  | 0.004 | 0.010 | 0.013 |
| Palladium crystal diameter (Å) | Before use | 330 | 305 | 294 |

TABLE 3

| | Comparative Example 5 | Example 9 |
|---|---|---|
| Halogen compound added | None | Ethyl bromate |
| Ethylbenzene conversion (mole %) at 3.5 hours | 26.8 | 14.3 |
| 17 hours | 35.3 | 28.8 |
| 33 hours | 33.7 | 29.6 |
| 100 hours | 23.7 | 29.9 |
| Styrene selectivity (mole %) at 3.5 hours | 97.1 | 96.0 |
| 17 hours | 96.8 | 96.6 |
| 33 hours | 96.6 | 97.1 |
| 100 hours | 86.4 | 97.0 |
| Benzene ring decomposition ratio (mole %) at 3.5 hours | 1.3 | 2.7 |
| 17 hours | 2.0 | 2.3 |
| 33 hours | 2.6 | 1.8 |
| 100 hours | 12.3 | 1.6 |
| $V_{min}$ | — | 0.011 |
| Palladium crystal diameter (Å) Before use | — | 461 |

EXAMPLE 17

Ruthenium chloride (anhydrous) in an amount required to give the catalyst composition shown in Table 4 was dissolved in a hydrochloric acid aqueous solution of palladium chloride in an amount required to deposit 2 parts by weight of metallic palladium on 100 parts of commercially available γ-alumina (B-19, a product of Fujimi Kenmazai Kabushiki Kaisha; particle diameter 1.5 mm). The catalyst composition was the same as in Examples 1 to 16 in regard to the indication of KBr-Pd-$Al_2O_3$, and the amounts of other elements added were expressed in moles per mole of the palladium deposited.

The γ-alumina was impregnated with the resulting mixed solution of the metal compounds, dried under reduced pressure at 50° C. by a rotary evaporator, and dried in air at 110° C. The resulting composition was filled into a quartz reaction tube, reduced in a stream of steam at 500° C. for 4 hours, and cooled to room temperature in a stream of nitrogen. The resulting composition was treated in a muffle furnace at 1130° C. for 4 hours. The composition was dipped in a 0.25 N aqueous solution containing potassium bromide in an amount to give the composition shown in Table 4, dried under reduced pressure at 50° C. using a rotary evaporator, and dried at 110° C. for 16 hours. The resulting composition was packed into a stainless steel reaction tube, and treated in a stream of air at 350° C. for 7 hours. The same reaction tube as used in Example 6 was filled with 12.7 ml of the catalyst, and reaction was performed under the reaction conditions shown in Table 4. The results obtained are summarized in Table 4. The Vmin and palladium crystal diameter of the used catalyst are also shown in Table 4.

EXAMPLES 18 TO 30

Catalysts were prepared in the same way as in Example 17 except that the calcining temperature at the muffle furnace was changed to 1200° C. The added elements and their forms of compound, the reaction conditions, the reaction results, Vmin and palladium crystal diameter are shown in Table 4.

TABLE 4

| | | | | Reaction conditions | | | | |
|---|---|---|---|---|---|---|---|---|
| Example | Catalyst composition (omitting $100Al_2O_3$) | Metal salt added | Type of reactor | Temperature (°C.) | Total reaction time (hours) | mole/mole $H_2O/EB$ | $O_2/EB$ | HBr (ppm) | C.C.-starting materials/ C.C.-catalyst/hr |

| Example | Catalyst composition | Metal salt added | Type of reactor | Temp (°C) | Total time (hrs) | $H_2O/EB$ | $O_2/EB$ | HBr (ppm) | C.C. ratio |
|---|---|---|---|---|---|---|---|---|---|
| 17 | 1KBr-0.01Ru-2Pd | $RuCl_3$ | Example 6 | 320 | 43.0 | 3.28 | 0.67 | 11 | 914 |
| | | | | 340 | 139.0 | 4.71 | 1.38 | 10 | 1010 |
| 18 | 3KBr-0.01Pt-2Pd | $H_2PtCl_6$ | Example 1 | 343 | 120.2 | 3.85 | 0.73 | 11 | 1117 |
| 19 | 1KBr-1Zn-2Pd | $ZnCl_2$ | Example 6 | −330 | 46.0 | 5.56 | 0.71 | 4.2 | 1186 |
| | | | | 350 | 117.5 | 5.62 | 0.72 | 4.2 | 1200 |
| 20 | 1KBr-0.3Cr-2Pd | $Cr(NO_3)_3.9H_2O$ | Example 6 | 330 | 46.0 | 5.03 | 0.73 | 4.4 | 1147 |
| 21 | 1KBr-0.3Co-2Pd | $CoCl_2.6H_2O$ | Example 6 | 350 | 99.0 | 5.57 | 0.73 | 4.2 | 1212 |
| 22 | 1KBr-1Ni-2Pd | $Ni(NO_3)_2.6H_2O$ | Example 6 | 330 | 227.0 | 3.25 | 0.73 | 10 | 942 |
| 23 | 1KBr-0.01Pt-1Zn-2Pd | $H_2PtCl_6.ZnCl_2$ | Example 6 | 330 | 165.5 | 3.77 | 1.33 | 9.8 | 970 |
| | (After 165.5 hours, HBr concentration was changed to 30 ppm.) | | | 320 | 257.0 | 3.80 | 1.30 | 30 | 997 |
| | (After 257 hours, HBr concentration was changed to 10 ppm.) | | | 330 | 425.0 | 3.78 | 2.02 | 10 | 1300 |
| 24 | 1KBr-0.1Sr-1Zn-2Pd | $SrCl_2.ZnCl_2$ | Example 1 | 352 | 95.6 | 3.25 | 0.68 | 10 | 990 |
| 25 | 1KBr-0.001Pt-1Zn-2Pd | $H_2PtCl_6.ZnCl_2$ | Example 6 | 330 | 307.0 | 3.29 | 1.05 | 2.3 | 1274 |
| 26 | 2KBr-0.001Cr-1Zn-2Pd | $Cr(NO_3)_3.9H_2O.ZnCl_2$ | Example 1 | 327 | 170.9 | 3.19 | 0.78 | 5.0 | 925 |
| | | | | 328 | 239.0 | 3.77 | 0.82 | 5.0 | 964 |
| 27 | 1KBr-0.01Cr-1Zn-2Pd | $Cr(NO_3)_3.)H_2O.ZnCl_2$ | Example 6 | 330 | 307.0 | 3.22 | 1.01 | °2.3 | 1171 |
| 28 | 0.5KBr-0.01Cr-1Zn-2Pd | $Cr(NO_3)_3.9H_2O.ZnCl_2$ | Example 1 | 333 | 362.0 | 2.95 | 0.74 | 2.5 | 1024 |
| 29 | 1KBr-0.3Cr-0.3Zn-2Pd | $Cr(NO_3)_3.9H_2O.ZnCl_2$ | Example 6 | 320 | 187.0 | 2.92 | 0.72 | 2.5 | 871 |
| 30 | 1KBr-0.3Fe-1Zn-2Pd | $FeCl_3.6H_2O.ZnCl_2$ | Example 6 | 320 | 91.0 | 3.33 | 1.70 | 1.6 | 1538 |

| | Reaction results (mole %) | | | Catalyst properties after use | |
|---|---|---|---|---|---|
| Example | Ethylbenzene conversion | Styrene selectivity | Benzene ring decomposition ratio | $V_{min}$ | Palladium crystal diameter (Å) |
| 17 | 47.4 | 91.4 | 7.8 | 0.023 | 272 |
| | 62.2 | 80.0 | 18.9 | | |
| 18 | 38.9 | 95.9 | 3.3 | 0.001 | 351 |
| 19 | 47.4 | 97.2 | 2.1 | 0.0 | 333 |
| | 55.4 | 91.9 | 7.3 | | |
| 20 | 39.6 | 98.2 | 1.1 | 0.002 | 317 |
| 21 | 37.8 | 98.0 | 1.3 | 0.0 | 356 |
| 22 | 48.1 | 96.5 | 2.6 | 0.0 | 377 |
| 23 | 69.1 | 81.2 | 18.1 | 0.0 | 329 |

TABLE 4-continued

|    |      |      |      |       |     |
|----|------|------|------|-------|-----|
|    | 31.8 | 98.3 | 1.3  |       |     |
|    | 56.1 | 94.3 | 4.9  |       |     |
| 24 | 44.7 | 97.7 | 1.5  | 0.0   | 343 |
| 25 | 48.3 | 96.6 | 2.6  | 0.004 | 321 |
| 26 | 51.5 | 96.5 | 2.8  | 0.0   | 334 |
|    | 54.7 | 95.3 | 4.0  |       |     |
| 27 | 56.4 | 95.1 | 3.9  | 0.0   | 326 |
| 28 | 49.0 | 94.8 | 4.4  | 0.0   | 322 |
| 29 | 49.1 | 96.7 | 2.3  | 0.0   | 299 |
| 30 | 64.2 | 82.0 | 17.0 | 0.008 | 337 |

EXAMPLE 31

A catalyst having the composition 1KBr-1Mg-1Zn-2Pd-100Al$_2$O$_3$ was prepared using MgCl$_2$.6H$_2$O and ZnCl$_2$ by the same catalyst preparing method as in Example 17 except that the calcining temperature in the muffle furnace was changed to 1200° C.

The same reaction tube as used in Example 6 was charged with 12.7 ml of the catalyst, and reaction was performed under the following conditions:
Steam oxygen (air) ethylbenzene=3.49/1.34/1 (mole/mole)
GHSV=1392 hr$^{-1}$
HBr=3.6 ppm
Reaction temperature=320° C.

Between 185 hours and 188 hours after the initiation of the reaction, an ethylbenzene conversion of 62.2 mole%, a styrene selectivity of 84.4 mole% and a benzene ring decomposition ratio of 14.8 mole% were obtained. After 190 hours, nitrogen was also introduced in addition to the air, and the reaction was continued under the following reaction conditions:
Steam/oxygen (air)/nitrogen/ethylbenzene=9.98/2.7/26.3/1 (mole/mole)
HBr=2.5 ppm
Reaction temperature=300° C.
GHSV=2130 hr$^{-1}$ Between 257 and 260 hours after the initiation of the reaction, an ethylbenzene conversion of 68.7 mole%, a styrene selectivity of 87.4 mole%, and a benzene ring decomposition ratio of 12.2 mole% were obtained.

EXAMPLE 32

A catalyst having the composition 1KBr-1Ba-1Zn-2Pd-100Al$_2$O$_3$ was prepared by using BaCl$_2$ and ZnCl$_2$ in the same way as in Example 31.

The same reaction tube as used in Example 6 was packed with 12.7 ml of the catalyst, and reaction was performed under the following conditions:
Steam oxygen (air)/ethylbenzene=2.90/1.13/1 (mole/mole)
GHSV=1167 hr$^{-1}$
HBr=4.3 ppm
Reaction temperature=320° C.

Between 185 hours and 188 hours after the initiation of the reaction, an ethylbenzene conversion of 66.4 mole%, a styrene selectivity of 89.9 mole% and a benzene ring decomposition ratio of 9.1 mole% were obtained. After 190 hours, nitrogen was also introduced in addition to the air. The reaction was continued under the following conditions:
Steam/oxygen (air)/nitrogen/ethylbenzene=9.35/3.1/27.5/1 (mole/mole)
GHSV=1957 hr$^{-1}$
HBr=2.6 ppm
Reaction temperature=300° C.

Between 257 hours and 260 hours after the initiation of the reaction, an ethylbenzene conversion of 74.3 mole%, a styrene selectivity of 87.2 mole% and a benzene ring decomposition ratio of 12.3 mole% were obtained.

After 408 hours, the HBr content was increased to 14.7 ppm. The reaction was continued under the following conditions:
Steam/oxygen (air)/nitrogen/ethylbenzene=9.35/3.1/27.5/1 (mole/mole)
GHSV=1957 hr$^{-1}$
HBr=14.7 ppm
Reaction temperature=320° C.

Between 521 hours and 260 hours after the initiation of the reaction, an ethylbenzene conversion of 57.7 mole%, a styrene selectivity of 99.1 mole% and a benzene ring decomposition ratio of 0.7 mole% were obtained.

What we claim is:

1. A process for producing an alkenyl-substituted aromatic compound by the oxidative dehydrogenation of the corresponding alkyl-substituted aromatic compound which comprises catalytically reacting at a temperature in the range of about 200° C. to about 400° C. an alkyl-substituted aromatic compound in the vapor phase in the presence of molecular oxygen and a catalyst composed of palladium metal having a crystal size of about 200 Å, a metal halide compound and at least one promotor selected from the group consisting of elements of Groups Ia, IIa, IIb and VIa of the periodic table, and elements of Group VIII of the periodic table other than palladium to convert said alkyl substituted aromatic compound to the corresponding alkenyl-substituted aromatic compound wherein said palladium metal, metal halide compound and promotor element are supported on an alumina carrier containing at least 80% by weight of the total alumina of α-alumina wherein the alumina carrier has a pore volume ratio (Vmin), expressed by the following equation $$V\text{min} = V_A/(V_A + V_B)$$

wherein $V_A$ is the volume (ml/g) of pores which require a penetration pressure by the mercury penetration method of 6,000 psi to 60,000 psi, and $V_B$ is the volume (ml/g) of pores which require a penetration pressure of 900 psi to less than 6,000,
of not more than 0.2 said reaction being carried out in the presence of a compound selected from the group consisting of bromine compounds and chlorine compounds which are gaseous under the reaction conditions and in an amount of 0.1 to less than 50 ppm as its concentration in the mixture of the alkyl-substituted aromatic compound gas and the molecular oxygen-containing gas.

2. The process of claim 1 wherein the pore volume ratio (Vmin) is not more than about 0.15.

3. The process of claim 1 wherein the metal halide compound is a metal bromide.

4. The process of claim 1 wherein the alkyl-substituted aromatic compound is ethylbenzene, and the alkenyl-substituted aromatic compound is styrene.

5. The process of claim 1 wherein said bromine compounds and chlorine compounds are used in an amount of about 1 to 30 ppm.

6. The process of claim 1, wherein the reaction temperature is about 250° to 350° C.

7. The process of claim 1 wherein at least 90% by weight of the alumina carrier is alpha-alumina.

8. The process of claim 1 wherein the palladium metal has a crystal size of about 300 Å to about 550 Å.

9. The process of claim 1 wherein the palladium metal has a crystal size of about 400 Å to about 500 Å.

10. The process of claim 1 wherein the molar ratio of the metal halide compound to palladium is in the range of about 0.1 to 1 to 20 to 1.

11. The process of claim 1 wherein the promotor element is present at an atomic ratio of promotor element to palladium of from about 0.0001:1 to about 100:1.

12. The process of claim 1 wherein the promotor element is present at an atomic ratio of promotor element to palladium of from about 0.001:1 to about 5:1.

13. A process for producing styrene by the oxidative dehydrogentation of ethylbenzene which comprises catalytically reacting at a temperature in the range of about 200° C. to about 400° C. ethylbenzene in the vapor phase in the presence of molecular oxygen and a catalyst consisting essentially of palladium metal having a crystal size of about 300 Å to about 550 Å, a metal bromide compound, and at least one promotor element selected from the group consisting of elements of Groups Ia, IIa, IIb and VIa of the periodic table, and elements of Group VIII of the periodic table other than palladium, said palladium metal, metal bromide compound and promotor element being supported on an alumina carrier containing at least 85% by weight of the total alumina of alpha-alumina wherein the alumina carrier has a pore volume ratio (Vmin), expressed by the following equation $$V\text{min} = V_A/(V_A + V_B)$$

wherein $V_A$ is the volume (ml/g) of pores which require a penetration pressure by the mercury penetration method of 6,000 psi to 60,000 psi, and $V_B$ is the volume (ml/g) of pores which require a penetration pressure of 900 psi to less than 6,000, of not more than about 0.15, the molar ratio of metal bromide to palladium being in the range of about 0.25:1 to about 10:1, and the molar ratio of the promotor element to palladium being in the range of from about 0.001:1 to about 10:1, said reaction being carried out in the presence of a compound selected from the group consisting of bromine compounds and chlorine compounds which are gaseous under the reaction conditions and in an amount of from about 1 to about 30 ppm as its concentration in the mixture of ethylbenzene and the molecular oxygen-containing gas.

14. The process of claim 13 wherein the mole ratio of oxygen to ethylbenzene is in the range of about 0.1:1 to about 5:1.

15. The process of claim 13 wherein the mole ratio of oxygen to ethylbenzene is in the range of about 0.25:1 to about 5:1.

16. The process of claim 13 wherein said reaction is carried out in the presence of steam in a mole ratio of steam to ethylbenzene of up to about 20:1.

17. The process of claim 16 wherein the steam/ethylbenzene mole ratio is from about 0.5:1 to about 10:1.

18. A process for producing an alkenyl-substituted aromatic compound by the oxidative dehydrogenation of the corresponding alkyl-substituted aromatic compound which comprises catalytically reacting at a temperature in the range of about 200° C. to about 400° C. an alkyl-substituted aromatic compound in the vapor phase in the presence of molecular oxygen and a catalyst composed of palladium metal having a crystal size of about 200 Å, and metal halide compound to convert said alkyl substituted aromatic compound to the corresponding alkenyl-substituted aromatic compound wherein said palladium metal and metal halide compound are supported on an alumina carrier containing at least 80% by weight of the total alumina of α-alumina wherein the alumina carrier has a pore volume ratio (Vmin), expressed by the following equation $$V\text{min} = V_A/(V_A + V_B)$$

wherein $V_A$ is the volume (ml/g) of pores which require a penetration pressure by the mercury penetration method of 6,000 psi to 60,000 psi, and $V_B$ is the volume (ml/g) of pores which require a penetration pressure of 900 psi to less than 6,000, of not more than 0.2 said reaction being carried out in the presence of a compound selected from the group consisting of bromine compounds and chlorine compounds which are gaseous under the reaction conditions and in an amount of 0.1 to less than 50 ppm as its concentration in the mixture of the alkyl-substituted aromatic compound gas and the molecular oxygen-containing gas.

* * * * *